United States Patent [19]

Delmore et al.

[11] Patent Number: 5,506,185
[45] Date of Patent: Apr. 9, 1996

[54] CERAMIC OXYANION EMITTER

[75] Inventors: James E. Delmore; Anthony D. Appelhans; Eric S. Peterson, all of Idaho Falls, Id.

[73] Assignee: Lockheed Idaho Technologies Company, Idaho Falls, Id.

[21] Appl. No.: 265,489

[22] Filed: Jun. 24, 1994

[51] Int. Cl.$^6$ .................................................. C04B 35/50
[52] U.S. Cl. .......................... 501/152; 252/518; 252/521
[58] Field of Search ................. 374/8, 126; 252/500, 252/501.1, 512, 517, 518, 521; 501/152

[56] References Cited

U.S. PATENT DOCUMENTS 5,111,108   5/1982   Goodman et al. ................... 252/521

OTHER PUBLICATIONS

Delmore, J. E., et al, "Tube Ion Source for the Study of Chemical Effects in Surface Ionisation," *International Journal of Mass Spectrometry and Ion Processes*, 108 (1991) pp. 179–181 no month.

Delmore, J. E., "Rare Earth Oxide Catalyzed Oxidation of Rhenium to ReO$_3$—As Observed by Negative Surface Ionization Mass Spectrometry," *The Journal of Physical Chemistry*, (1987), 91, pp. 2883–2886 no month.

Primary Examiner—Mark L. Bell
Assistant Examiner—Paul Marcantoni
Attorney, Agent, or Firm—Hopkins Roden Crockett Hansen & Hoopes

[57] ABSTRACT

A rare earth oxide matrix (composition of matter) is formed which emits (upon heating) heavy metal oxide anions (oxyanions) into a gas phase, wherein the anions are emitted with high intensity, and wherein longevity of life of the composition of matter is retained. The matter is formed by blending a major component of a rare earth oxide, Europium oxide (Eu$_2$O$_3$) or Ytterbium oxide (Yb$_2$O$_3$), with a minor component of a Barium (Ba), Calcium (Ca) or Strontium (Sr) salt of a heavy metal oxyanion. Heavy anions are emitted upon heating the composition of matter to a predetermined temperature of about 800° C.

2 Claims, No Drawings

CERAMIC OXYANION EMITTER

CONTRACTUAL ORIGIN OF THE INVENTION

The United States Government has rights in this invention pursuant to Contract No. DE-AC07-76ID01570 between the United States Department of Energy and EG&G Idaho, Inc.

TECHNICAL FIELD

This invention relates in general to a composition of matter and method of producing ions, and in particular to an oxyanion emitting composition of matter and method for producing such anions into a gas phase.

BACKGROUND OF THE INVENTION

Ion emitting materials are useful in ion guns for bombarding materials. Ion emitting materials are also used in analytical instruments, and may be used for other applications such as ion implantation.

Currently, however, there are no solid state ion sources which emit heavy negative ions (anions). The solid state ion sources in current commercial use all emit positive ions (cations). There are gas-fed ion guns which can be used to produce primarily positive ions but can also be used to produce the oxygen negative ion. These gas-fed ion guns have the disadvantage of loading the vacuum system with gas that must be pumped from the system, preventing operation at high vacuum. The gas guns can be used to produce the oxygen negative ion, but this anion has the disadvantage of being very light in mass, i.e., 16, whereas heavier ions are much more efficient for sputtering secondary ions of organic molecules from surfaces.

The existing problem with prior art ion producing materials is the inherent limitations of the materials themselves. Namely, ion emissions have typically been too low to be commercially viable in ion guns. Furthermore, the life span of the materials is short because the intensity of the ion emissions decreases over time when heated at sufficiently high temperatures to produce ion emissions. As the intensity of the ion emissions decreases over time due to the applied heat, it is necessary to apply more heat to keep the intensity of emissions up. However, as more heat is applied, the life of the materials is shortened even more, and the intensity of emissions decreases even sooner. This process typically results in short-lived ion-producing materials.

Accordingly, a main objective of the present invention is to provide a high intensity, long lasting anion emitting capable composition of matter and method for producing heavy anion emissions.

SUMMARY OF THE INVENTION

According to principals of the present invention in its preferred embodiment, a material is prepared which has a rare earth oxide as its major component, and as its minor component an oxyanion as a Barium (Ba), Calcium (Ca), or Strontium (Sr) salt. This material is blended and sintered, pressed into an open faced container, and heated to within a predetermined range to emit oxyanions therefrom. Relative to prior art materials, the present invention emits anions with a higher intensity over a longer period of time.

According to further principles of the present invention, the chemical environment inside this composition of matter prevents the loss of the heavy metal oxide anions prematurely: 1) from unwanted chemical reductions, by having an oxidizing environment inside these materials to maintain the anion in its highest oxidation state; and 2) by having a counter ion to the oxyanion which prevents low temperature volatilization of the oxyanion.

Finally, this composition is formed such that it maintains its original structural shape upon heating to the temperatures which result in oxyanion emission.

DETAILED DESCRIPTION OF THE INVENTION

A composition of matter, for emitting heavy anions into a gas phase upon heating, is formed having two components. The major component is a rare earth oxide, and the minor component is a Calcium (Ca), Barium (Ba) or Strontium (Sr) salt of the heavy metal oxide anion, as follows:

a. one part $R_1(R_2)_2$; and
b. a plurality of parts $(R_3)_2O_3$; wherein $R_1$ is Ba, Ca or Sr, $R_2$ is a mono-valent oxyanion, and $R_3$ is the rare earth element Europium (Eu) or Ytterbium (Yb).

As noted, the major component is the rare earth oxide Europium oxide ($Eu_2O_3$) or Ytterbium oxide ($Yb_2O_3$). The minor component is a Barium, Calcium or Strontium salt of the heavy metal oxide anion (oxyanion) such as Rhenium Tetroxide (perrhenate, $ReO_4^-$). Perrhenate has a heavy mass of 250.

Significant testing reveals that Barium perrhenate [$Ba(ReO_4)_2$] and Calcium perrhenate [$Ca(ReO_4)_2$] provide similar results as the minor component. However, Barium provides the preferred embodiment. Although not tested, it is presupposed that Strontium perrhenate [$Sr(ReO_4)_2$] would provide similar results due to the existence of Sr between Ca and Ba in Group II on the Periodic table of elements.

Also in its preferred embodiment, one part $Ba(ReO_4)_2$ powder is blended with sixteen (16) parts of $Eu_2O_3$ powder to form a mixture. Alternatively, eight (8) to sixteen (16) parts of $Eu_2O_3$ has proven satisfactory. Although it is recognized that any plurality of parts of $Eu_2O_3$ form a suitable oxyanion emitting composition (i.e., such as fewer than eight or more than sixteen), eight to sixteen parts has tested better, with sixteen testing the best.

The heavy metal oxyanion $ReO_4$ has also tested the best. However, it is also recognized that other oxyanions such as Manganese Tetroxide (permanganate, $MnO_4^-$) or Tungsten trioxide ($WO_3^-$), produce an alternatively suitable composition.

After the major and minor component powders are blended into a mixture, the mixture is sintered at high temperatures (i.e., about 800° C.) to form a ceramic composition for ease of handling. Although this step is not required, it eases the handling of the composition for insertion and/or compaction into a suitable refractory device for heating of the composition to provide anion emissions.

Finally, the mixture or ceramic is heated to a predetermined temperature to produce the anion emissions. In its preferred embodiment, the heating temperature is about 800° C. Although it is recognized that temperatures ranging from 750° to 900° C. provide satisfactory results, the lower the temperature ranges, the intensity of ion emissions also lowers. On the other hand, the higher the temperature ranges, the ion emission intensity increases, but the life of the composition decreases. Thus, testing has proven that about 800° C. provides the preferred temperature for intense anion production balanced with longevity of life of the mixture.

For example, an ion emitter using a Europium oxide/Barium perrhenate [$Eu_2O_3,Ba(ReO_4)_2$] ceramic, 16/1 weight ratio, heated at a temperature of about 800° C., produced high intensity anion emissions for 11 months in a secondary ion mass spectrometer (SIMS) before replacement became necessary. This was achieved with a current ion source of from 100–150 pA for 40 hours per week for 11 months. Comparatively, previous materials only produced 40–50 pA of current ion source for 40 hours per week for only one month.

Calcium and Barium salts of the perrhenate anion have been tested with a variety of rare earth oxide matrices. However, the specific rare earths which when blended with a perrhenate salt produce materials with the best gas phase anion emission properties are those which have a predominantly +3 oxidation state but with an achievable +2 oxidation state (3,2 rare earths). These are Europium, Ytterbium, Samarium, and Thulium. Europium, Ytterbium, and Samarium have been tested in blends with Barium perrhenate and found to have high perrhenate anion emission rates, with Europium and Ytterbium in particular achieving especially high anion emission rates.

Perrhenate composition emitters were tested with perrhenate anions combined with a variety of cations. Calcium and Barium cations were by far superior for those which were tested. It is probable that all alkaline earth cations would produce good perrhenate salts for blending into these emitters. Melting points were measured for these materials, and it was found that the alkaline earth perrhenates had much higher melting points than any others tested, such as the alkali metal cations. By increasing the melting point the perrhenate can be retained in the emitter up to the point where perrhenate anions can sublime from the surface.

The emitters which demonstrate the longest lifetimes are those prepared from Europium and Ytterbium oxides, but even these fail if pushed too long or too hot. All the emitters tested eventually fail with use over time, particularly if they are heated to temperatures 100° C. higher than the optimum temperature of 800° C. The main reason these emitters fail is that perrhenate is reduced to a lower oxidation state with use ( i.e., less than +7).

The fact that 3,2 rare earth oxides make such good host compositions for the perrhenate appears to be that they are capable of providing an oxidizing environment for perrhenate. Since Europium and Ytterbium form the most stable +2 oxidation states for the rare earths, they in turn provide the best oxidizing environment for these materials, and experimentally are the best oxyanion emitters. Thus, the perrhenate anions are stabilized, which has Rhenium in its highest oxidation state, +7, so that the composition has greatly extended lifetimes in regards to perrhenate anion emission.

The most intense oxyanion emission enhancement effects are also noted for the same oxides of Europium and Ytterbium, which also have the most stable +2 oxidation states.

Although not yet proven, Europium and Ytterbium oxides may be superior matrices where a high temperature oxide matrix with an oxidizing environment is required.

Other 3,2 elements such as iron, with refractory oxides and stable +3 and +2 oxidation states (though not yet tested), may function equally well as host compositions for anion emission, and more generally as refractory matrices in which there is need for an oxidizing environment.

What has been described above are the preferred embodiments and methods of use for an oxyanion emitting composition of matter. It is clear that the present invention provides a powerful tool for emitting heavy anions with high intensity and longevity of life of the composition of matter. While the present invention has been described by reference to specific embodiments, it will be apparent that other alternative embodiments and methods of implementation or modification may be employed without departing from the true spirit and scope of the invention.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A composition of matter for emitting ions consisting essentially of a) one part $R_1(R_2)_2$; and b) eight to sixteen parts $(R_3)_2O_3$; wherein $R_1$ is selected from the group consisting of Barium, Calcium and Strontium, $R_2$ is selected from the group consisting of $ReO_4^-$, $MnO_4^-$, and $WO_3^-$, $R_3$ is selected from the group consisting of Europium and Ytterbium, and wherein respective $ReO_4^-$, $MnO_4^-$, and $WO_3^-$ anions are emitted by heating the composition at between 750° and 900° C.

2. A method of producing anion emissions consisting essentially of the steps of:

a. blending one part $R_1(R_2)_2$ with eight to sixteen parts $(R_3)_2O_3$ to form a mixture, wherein $R_1$ is selected from the group consisting of Barium, Calcium and Strontium, $R_2$ is selected from the group consisting of $ReO_4^-$, $MnO_4^-$, and $WO_3^-$, and $R_3$ is selected from the group consisting of Europium and Ytterbium; and b. heating the mixture at between 750° to 900° C.

* * * * *